US011235160B2

(12) United States Patent
Von Bergen et al.

(10) Patent No.: US 11,235,160 B2
(45) Date of Patent: Feb. 1, 2022

(54) ADAPTER TO ALLOW ELECTROGRAM VISUALIZATION AND PACING FROM TEMPORARY EPICARDIAL WIRES

(71) Applicant: Wisconsin Alumni Research Foundation, Madison, WI (US)

(72) Inventors: Nicholas Von Bergen, Middleton, WI (US); Philip Terrien, Madison, WI (US); Matthew Knoespel, Madison, WI (US); Connor Sheedy, Madison, WI (US); James Olson, Madison, WI (US); Randal Mills, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 270 days.

(21) Appl. No.: 16/677,098

(22) Filed: Nov. 7, 2019

(65) Prior Publication Data

US 2020/0069950 A1  Mar. 5, 2020

Related U.S. Application Data

(63) Continuation of application No. 15/229,371, filed on Aug. 5, 2016, now Pat. No. 10,471,261.

(51) Int. Cl.
*A61B 5/308* (2021.01)
*A61N 1/37* (2006.01)
(Continued)

(52) U.S. Cl.
CPC .............. *A61N 1/3702* (2013.01); *A61B 5/30* (2021.01); *A61B 5/339* (2021.01); *A61B 5/4836* (2013.01);
(Continued)

(58) Field of Classification Search
CPC .. A61N 1/3702; A61N 1/0587; A61N 1/0595; A61N 1/36514; A61B 5/30; A61B 5/339; A61B 5/4836
See application file for complete search history.

(56) References Cited

U.S. PATENT DOCUMENTS 4,149,527 A * 4/1979 Naylor ..................... A61B 5/30
600/510
4,832,041 A * 5/1989 Wang ....................... A61B 5/30
600/510

(Continued)

OTHER PUBLICATIONS

Hodam and Starr. "Temporary postoperative epicardial pacing electrodes. Their value and management after open-heart surgery." Ann Thorac Surg. Dec. 1969;8(6):506-10. (Year: 1969).*

(Continued)

*Primary Examiner* — Eugene T Wu
(74) *Attorney, Agent, or Firm* — Boyle Fredrickson S.C.

(57) ABSTRACT

A connector block that permits simultaneous and continuous interconnection of the three leads of the epicardial pacing wires, the pacemaker, and the ECG monitor on clear separately labeled connectors is provided. Circuitry is provided that allows the display of epicardial signals on the telemetry unit, while still preserving the ability to pace the heart from the pacemaker. When pacing the connector block prevents excessive loading of the pacer signals by the ECG monitor and/or damage to the monitor by the high-voltage pacer signals. The connector block may be used universally on all monitors without the need for sophisticated understanding of the electrical characteristics of the ECG monitor or concern for damage or improper signal loading.

20 Claims, 3 Drawing Sheets

(51) Int. Cl.
*A61N 1/05* (2006.01)
*A61B 5/00* (2006.01)
*A61B 5/30* (2021.01)
*A61B 5/339* (2021.01)
*A61N 1/365* (2006.01)

(52) U.S. Cl.
CPC ...... *A61N 1/0587* (2013.01); *A61B 2562/227* (2013.01); *A61N 1/0595* (2013.01); *A61N 1/36514* (2013.01)

(56) References Cited

U.S. PATENT DOCUMENTS

| | | | | |
|---|---|---|---|---|
| 5,666,958 | A | * | 9/1997 | Rothenberg ........... A61N 1/056 600/509 |
| 5,682,902 | A | * | 11/1997 | Herleikson ........... A61B 5/339 600/521 |
| 6,246,902 | B1 | | 6/2001 | Naylor et al. |
| 8,755,885 | B2 | | 6/2014 | Deno et al. |
| 2003/0040784 | A1 | * | 2/2003 | Pasternak ........... A61N 1/3752 607/116 |
| 2008/0058656 | A1 | | 3/2008 | Costello et al. |

OTHER PUBLICATIONS

Anjan S Batra et al.; "Post operative temporary epicardial pacing: When, how and why?." Annals of pediatric cardiology 1, No. 2 (2008): pp. 120-126. US.

Kurt Piggott et al.; "Intra-operative arrhythmia predicts post-operative arrhythmia and the need for temporary pacing wires." Cardiology in the Young 25, No. 03 (2014): pp. 1-5; US.

Bart Maesen et al.; "Post-operative atrial fibrillation: a maze of mechanisms." Europace 14, No. 2 (2012): pp. 159-174. Europe.

M.C. Reade; "Temporary epicardial pacing after cardiac surgery: a practical review." Anaesthesia 62, No. 3 (2007) pp. 264-271. US.

Yartsev, A.; "Anatomy of the Temporary Pacemaker Circuit"; retrieved from web-site: http:/www.derangedphysiology.com/main/core-topics-intensive-care/mechanical-haemodynamic-support; Chapter 2.5.2 / anatomy-temporary-pacemaker-circuit; pp. 1-4; US.

A. Kerkoff; "Definitions of Anatomy & Physiology [Online]", web-site: http://www.(livestrong.com/article/1 37578-definitions-anatomy-physiology); (Jan. 15, 2014). pp. 1-4; US.

J. Moini; "Anatomy and Physiology of the Cardiovascular System," in Anatomy and Physiology for Health Professionals, 2nd ed. Burlington, MA: Jones and Bartlett Publisher, 2016, ch. 5, sec. The Heart, pp. 37-40.; US.

Openstax College; "Cardiac Muscle and Electrical Activity". OpenStax—CNX module: m46664; (Mar. 20, 2013). web-site: https://cnx.org/content/m46664/1.3/; US.

Barbara J. Drew et al.; "Practice Standards for Electrocardiographic Monitoring in Hospital Settings an american heart association scientific statement from the councils on cardiovascular nursing, clinical cardiology, and cardiovascular disease in the young: Endorsed by the international society of computerized electrocardiology and the american association of critical-care nurses." Circulation 110, No. 17 (2004): pp. 2721-2746. US.

Allison V. Rosen et al.; "Common ECG lead placement errors. Part I: Limb lead reversals." International Journal of Medical Students 2, No. 3 (2014): pp. 92-98. US.

B.T. Bethea et al.; "Determining the utility of temporary pacing wires after coronary artery bypass surgery." The Annals of thoracic surgery 79, No. 1 (2005): pp. 104-107. US.

Yasir Abu-Omar et al.; "Indications and positioning of temporary pacing wires." Multimedia Manual of Cardio-Thoracic Surgery 2006, No. 0512 (2006); pp. 1-4: mmcts-2005. EP.

M. Manning; "Switch and Multiplexer Design Considerations for Hostile Environments"; web-site: www.analog.com/analogdialogue; Analog Dialogue 45-05, (May 2011). pp. 1-7; US.

"What is an Ideal Diode?"(n.d.).Retrieved Feb. 22, 2016, from http://www.learningaboutelectronics.com/Articles/Ideal-diode.php; pp. 1-8; US.

"Lessons in Electric Circuits"—vol. III. (n.d.). Retrieved Feb. 22, 2016, from littps://www.ibiblio.org/kuphaldt/electricCircuits/Seini/SEMI - 3 .html; pp. 1-69; US.

"Analog Devices". (n.d.). Retrieved Feb. 24, 2016, from http://www.analog.com/en/products/amplifiers/adc-drivers/full y-differential-amplifiers/ad8476.html; pp. 1-10; US.

Yueh-Tze Lan et al.; Postoperative arrhythmia. Current Opinion in Cardiology, 18(2), pp. 73-78; 2003; US.

Johann Auer et al.; Risk factors of postoperative atrial fibrillation after cardiac surgery. Journal of cardiac surgery, 20(5), pp. 425-431; 2005; Austria.

Bill Laumeister; Lightning Bolts, Defibrillators, and Protection Circuitry Save Lives; Webpage—Application Note 5724: http://www.maximintegrated.com/en/an5724; 2014 Maxim Integrated; pp. 1-7; US.

Adel S. Sedra et al.;"Microelectronic Circuits"; Book; Oxford University Press; pp. 1-8; 2015; US.

\* cited by examiner

ADAPTER TO ALLOW ELECTROGRAM VISUALIZATION AND PACING FROM TEMPORARY EPICARDIAL WIRES

CROSS REFERENCE TO RELATED APPLICATIONS

This application is a continuation of U.S. patent application Ser. No. 15/229,371, filed Aug. 5, 2016, hereby incorporated in its entirety by reference.

STATEMENT REGARDING FEDERALLY SPONSORED RESEARCH OR DEVELOPMENT

N/A

BACKGROUND OF THE INVENTION

The present invention relates to electrocardiographic (ECG) monitoring systems and, more specifically, to ECG monitoring systems that allow simultaneous pacing during electrogram visualization using epicardial pacing leads.

Telemetry monitoring allows medical professionals to monitor electrical activity of the heart in real time and for extended periods of time. Telemetry monitoring is often utilized after cardiac surgery, when patients are most at risk for arrhythmias. Abnormally slow or fast heart rhythms can cause increased morbidity and mortality in the patient. Atrial fibrillation is a common arrhythmia encountered postoperatively, although ventricular arrhythmias and conduction disturbances can also occur.

Atrial arrhythmias can be difficult for medical professionals to differentiate when monitoring surface ECG leads.

Due to this risk of postoperative arrhythmias, many patients have temporary epicardial pacing wires placed on the outside of their heart epicardium (outer layer of heart muscle) to permit pacing of the heart (via an artificial temporary pacemaker). The proximal ends of the epicardial pacing wires are normally wrapped and taped to the outer chest wall until needed for arrhythmia treatment.

Normally, cardiac rhythms are obtained from surface ECG electrodes placed on the patient's chest and viewed on bedside monitors. However, since atrial signals are not easily visualized using surface ECG electrodes, if the medical professional detects an irregularity, an ECG technician may be called to connect the epicardial pacing wires to an ECG monitor so that a medical professional can interpret the ECG signals with more accuracy (since the proximity of the recording wires to the atrial impulses greatly enhances atrial waveforms). If an arrhythmia is detected and the medical professional wishes to pace the heart, the epicardial pacing wires are detached from the ECG monitor and reconnected to a temporary pacemaker for pacing.

The process of connecting the epicardial pacing wires is time-consuming, and may need to be repeated for successive rounds of visualization and pacing. This also carries with it a risk of misconnection of three sets of wires from the ECG monitor, the pacemaker, and the epicardial connections.

SUMMARY OF THE INVENTION

The present invention provides a connector block that permits simultaneous and continuous interconnection of the three sets of wires of the epicardial pacing wires, the pacemaker, and the ECG monitor on clear, separately labeled connectors. As such, the connector block provides an intuitive and rapid interconnection system easily used in a hospital environment reducing procedure times and the chance of misconnection. By including circuitry to prevent excessive loading of the high-voltage pacer signals by the ECG monitor, the connector block may be used universally on all monitors without the need for sophisticated understanding of the electrical characteristics of the ECG monitor or concern for damage or improper signal loading.

Specifically, in one embodiment, the invention provides a connector box for connecting epicardial pacing leads of a patient to: (a) a pace generator which can analyze the rhythm and potentially deliver a pacing signal through the epicardial pacing leads to the heart of the patient and (b) a telemetry monitor receiving cardiac signals through the epicardial pacing leads from the heart of the patient, simultaneously to allow epicardial signals to be displayed on the monitor. The connector box includes first terminals for transmitting electrical cardiac signals to and from the epicardial pacing leads connected to the heart of the patient; second terminals for transmitting the epicardial signal to the pace generator and transmitting an electrical impulse to and from the pace generator; third terminals outputting a conditioned electrical signal to the telemetry monitor; and electrical circuitry connected with the first, second, and third terminals, which presents current division so the pacing current is propagated almost completely to the heart while the circuitry is receiving and conditioning the voltage potentials induced by the heart signal and the pacing signal with a clipper that limits the voltage sent to the monitor at at least one predetermined voltage level.

It is thus a feature of at least one embodiment of the invention to allow for simultaneous and continuous interconnection of epicardial pacing wires for pacing and diagnosis thus avoiding the cumbersome process of alternating the epicardial wires between pacemaker and telemetry.

The first, second, and third terminal may be labeled with an indicia identifying the epicardial leads, pacer generator, and telemetry monitor.

It is thus a feature of at least one embodiment of the invention to allow for intuitive and rapid connection of the appropriate connector to each terminal in the challenging environment of medical care.

In one embodiment, the connector box has a weight and a size adapted to be supported on the body of the patient.

It is thus a feature of at least one embodiment of the invention to reduce the risk of the wires from becoming dislodged from the epicardium due to pulling and maneuvering of the epicardial pacing wires. It is a further object of at least one embodiment of the invention to eliminate the need for extension leads on the epicardial wires.

Skin electrodes may be positioned on the body of the patient and received by the telemetry monitor to display both cardiac signals from the epicardial pacing leads and body electrodes.

It is thus a feature of at least one embodiment of the invention to permit simultaneous real-time monitoring of ventricular or atrial cardiac signals for improved rhythm discrimination and immediate analysis and feedback after pacing.

The first, second and third terminals may be mechanically releasable electrical connectors. The third terminals may have connectors matching those of skin electrodes positioned on the body. The connectors of the third terminals may be snaps providing attachment of the connector box to the telemetry monitor. It is thus a feature of at least one embodiment of the invention to use similar connectors (such as alligator clips or snaps) as used to connect surface electrodes to the telemetry monitor for increased adaptability.

The clipper may be an active clipping circuit using an operational amplifier. The active clipping circuit may provide a first gain multiplying circuit and a second dividing circuit and operates to clip by boosting the signal at the first gain multiplying circuit beyond the output voltage range of the first gain multiplying circuit. The clipping circuit may provide a first and second clipping voltage level and clips the current limited combination signal if it exceeds the first clipping voltage level or is less than the second voltage clipping level.

It is thus a feature of at least one embodiment of the invention to maintain the scale necessary to monitor the ECG signals from becoming skewed by the pacing spikes and to protect the monitor from high voltage damage.

A passive clipping circuit may provide back-to-back diodes shunting the current limited combination signal. A low pass filter may filter high-frequency signals from the current limited combined signal.

It is thus a feature of at least one embodiment of the invention to condition the voltage potentials induced by the combined heart signal and pacing signal to limit the current entering the clipping circuit while preserving the battery life.

The present invention also facilitates a telemetry monitoring system to read the signals from the connecting epicardial leads of a patient, while also connecting to a pace generator adapted to allow a pacing signal through the epicardial pacing leads to a heart of the patient if needed. The system includes a telemetry monitor receiving cardiac signals through the epicardial pacing leads from the heart of the patient simultaneous with delivery of the pacing signal; and a connector box having first terminals for transmitting electrical cardiac signals to and from the epicardial pacing leads connected to the heart of the patient; second terminals for transmitting the electrical cardiac signals to the pace generator and transmitting an electrical impulse to and from the pace generator; third terminals outputting a conditioned electrical signal to the telemetry monitor; and electrical circuitry communicating with the first, second, and third terminals and providing a current limiter steering the electrical impulse predominantly to the heart of the patient and not to the electrical circuitry and receiving voltage signals induced by the heart; and a clipper limiting the voltage signals sent to the telemetry monitor at at least one predetermined voltage level.

The telemetry monitor has two connectors to the device, currently labeled as (LA) position input and a right arm (RA) position input, though other electrode position inputs could be utilized depending on the monitor. These connectors attach to the appropriate telemetry leads to transfer the conditioned electrical signal into the LA and RA telemetry inputs, or other electrode position inputs as necessary.

It is thus a feature of at least one embodiment of the invention to adopt the connector box for use with any telemetry monitor system to display an atrial electrogram (AEG) using atrial epicardial connections on the telemetry.

The epicardial pacing leads are connected to the atrium or ventricle of the patient.

It is thus a feature of at least one embodiment of the invention to provide improved atrial signals for differentiating atrial and junctional arrhythmias when P waves are not clearly visible from the surface electrode ECG.

The present invention also provides a method of delivering cardiac signals to a telemetry monitor and delivering pacing signals to a patient simultaneously utilizing a connector box with a first terminal for transmitting electrical signals to and from epicardial pacing leads connected to an epicardium of the heart; a second terminal for transmitting the electrical cardiac signals to the pace generator and transmitting an electrical impulse to and from a pace generator; a third terminal outputting a conditioned electrical signal to the telemetry monitor; and electrical circuitry communicating with the first, second, and third terminal and providing a current limiter steering the electrical impulse predominantly to the heart of the patient and not to the electrical circuitry and receiving voltage signals induced by the heart; and a clipper limiting the voltage sent to the telemetry monitor at at least one predetermined voltage level, the method including the steps of: connecting epicardial pacing leads to the first terminal; connecting a pacemaker connector to the second terminal; and connecting the telemetry monitor to the third terminal.

These particular objects and advantages may apply to only some embodiments falling within the claims and thus do not define the scope of the invention.

DETAILED DESCRIPTION OF THE PREFERRED EMBODIMENT

Figure 1:
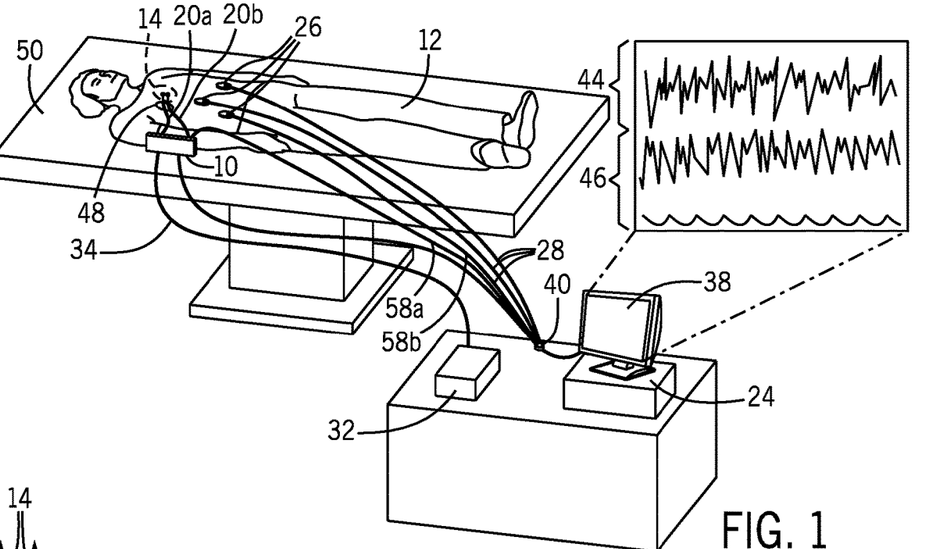
FIG. 1 is a perspective view of an adaptor of the present invention positioned between epicardial pacing wires sutured to the patient and medical devices requiring access to those epicardial pacing wires.

Referring now to FIG. 1, the connector block 10 of the present invention may provide a hub between a patient 12 and multiple medical devices including a pulse generator 32 delivering pacing signals to the patient 12 and a telemetry monitoring system 24 for visualizing cardiac signals 44, 46 of a heart 14 of the patient 12.

The patient 12 may be supported on a patient bed or table 50 in a hospital environment, for example, in a surgical room following cardiac surgical procedure. The connector block 10 may be conveniently positioned near the patient 12, such as mounted to the patient bed or table 50 to provide a stable connection point in close proximity to the patient 12. Alternatively, and preferably, the connector block 10 may have a size and weight, which allows it to be taped or otherwise adhered to the patient's chest or body to avoid dislodgement or accidental removal of the patient connections. For example, the connector block 10 may have an adhesive backing, which it stuck directly onto the patient's chest or body.

Figure 2:
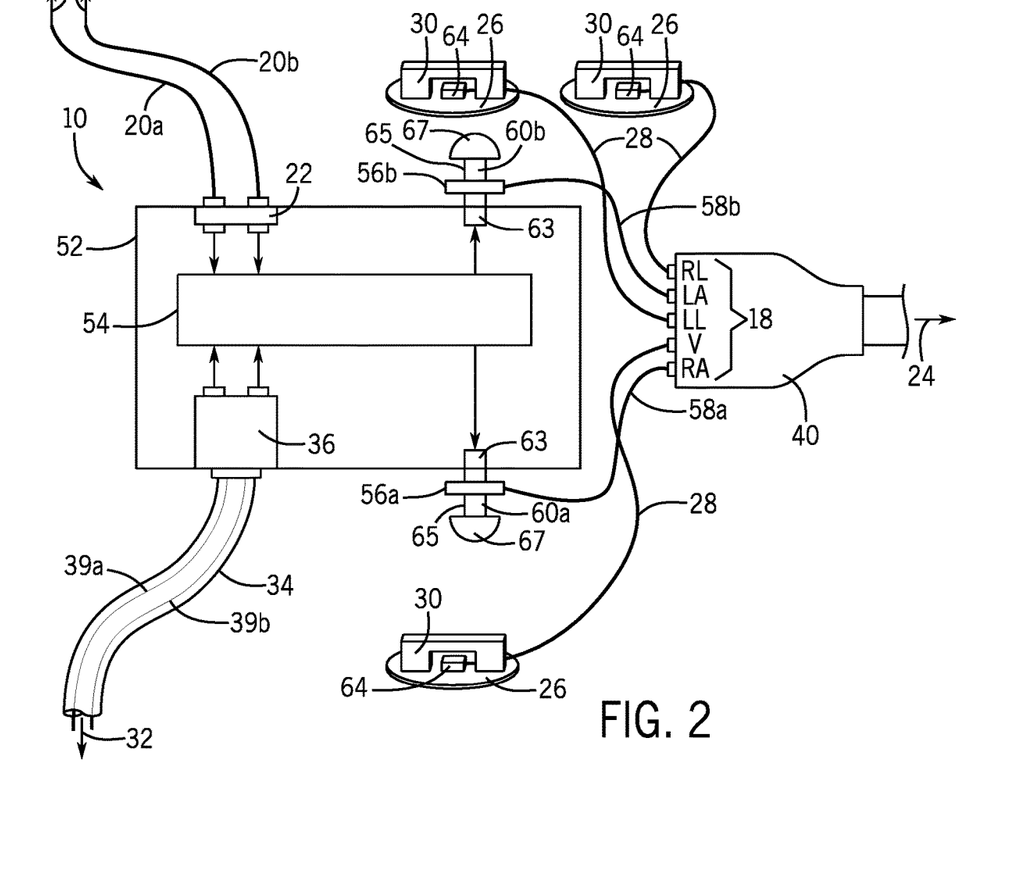
FIG. 2 is a simplified block diagram of one embodiment of the present invention showing the adaptor communicating between the epicardial pacing wires, a pacemaker and a 5-electrode telemetry monitor.

Referring now also to FIG. 2, a first connection is made to the patient 12 by placing epicardial pacing wires 20a, 20b directly on an epicardium of the heart 14 of the patient 12. The epicardial pacing wires 20a, 20b are typically installed during surgery, with small electrode needle tips on one end sutured into the atrial epicardium of the heart 14 and larger needles on the other end penetrating the body wall and exiting the skin at puncture wound 48 in the chest, bringing the epicardial pacing wires 20a, 20b to the surface of the skin. For example, in a bipolar circuit a positive electrode and negative electrode may be placed in each chamber of the heart 14, typically the right atrium and/or right ventricle. The positive electrode and negative electrode may be found on two separate wires or on a single wire with the electrodes typically placed about 8 mm apart (for example, Medtronic Bipolar Coaxial 6495).

In the exemplary embodiment, the positive and negative electrodes are epicardial pacing wires 20a and 20b, respectively, placed at the right atrium of the heart 14 to serve the dual purpose of atrial pacing and atrial visualization as described below. The epicardial pacing wires 20 then extend from the patient 12 and connect to the external connector block 10 to allow for these dual functions to operate simultaneously.

During pacing, the epicardial pacing wires 20a, 20b are used to deliver a small electrical current from the negative electrode to the positive electrode to activate myocardial cells of the heart 14. A pulse generator 32 may be connected to the connector block 10 to thereby deliver this electrical current to the epicardial pacing wires 20a, 20b. For example, the pulse generator 32 may deliver a ventricular pacing impulse to the ventricle of the heart or deliver an atrial pacing impulse to the right atrium of the heart. The source of the pacing energy is typically a rechargeable or replaceable battery in the pulse generator 32. In the exemplary embodiment, the pulse generator 32 delivers an atrial pacing impulse to the connector box 10 which in turn is delivered to the epicardial pacing wires 20a, 20b connected to the right atrium of the heart 14. Atrial signals from the heart 14 may return through the epicardial pacing wires 20a, 20b and be delivered to the pulse generator 32 which then applies processing algorithms to the atrial signals to determine a proper pacing prescription. The pulse generator 32 may be, for example, Medtronic 5392, 5391, 5348, 5388 Dual Chamber Temporary Pacemakers.

During visualization, the epicardial pacing wires 20a, 20b are able to transmit changes in electric potential between the positive and negative electrodes during cardiac rhythm. In the exemplary embodiment, the connector block 10 receives these electrical heart signals and conditions these signals, which is in turn delivered to the telemetry monitoring system 24 for atrial visualization as further described below.

A second connection is made to the patient 12 by placing multiple surface ECG electrodes 26 on a body of the patient 12. The surface ECG electrodes 26 are used to detect the electrical changes on the skin that arise from the heart's depolarization during cardiac rhythm. For example, the surface ECG electrodes 26 are placed at known body positions for a 3-electrode system (3-lead ECG), 5-electrode system (5-lead ECG) and 10-electrode system (12-lead ECG).

Referring still to FIG. 2, in the illustrated embodiment, three ECG electrodes 26 are attached to the patient 12. The surface ECG electrodes 26 may provide conductive gel pads that are adhered to the body of the patient 12 with outwardly protruding buttons 64 that "snap on" to fasteners 30 of three ECG cables 28, respectively, which can deliver the surface ECG signals directly to the telemetry monitoring system 24.

The telemetry monitoring system 24 may allow for real time visualization of the cardiac signals from the patient 12 by displaying the signals on a monitor 38 for analysis by the medical professional. The signals from the multiple surface ECG electrodes 26 are delivered through the multiple ECG cables 28 directly to the telemetry monitoring system 24, which receives the ECG cardiac signals and displays them on the monitor 38. In contrast, the leads from the epicardial pacing wires 20a, 20b may connect through the connector block 10 which may then deliver the conditioned epicardial signals to the telemetry monitoring system 24. In this manner the telemetry monitoring system 24 may allow both the surface ECG electrode waveforms 46 and epicardial waveforms 44 to be viewed simultaneously on the monitor 38. It is understood that other patient parameters may be displayed on the monitor 38 or be monitored by the telemetry monitoring system 24, such as peripheral pulse oximetry, blood pressure, respiratory rate, body temperature, etc.

Figure 3:
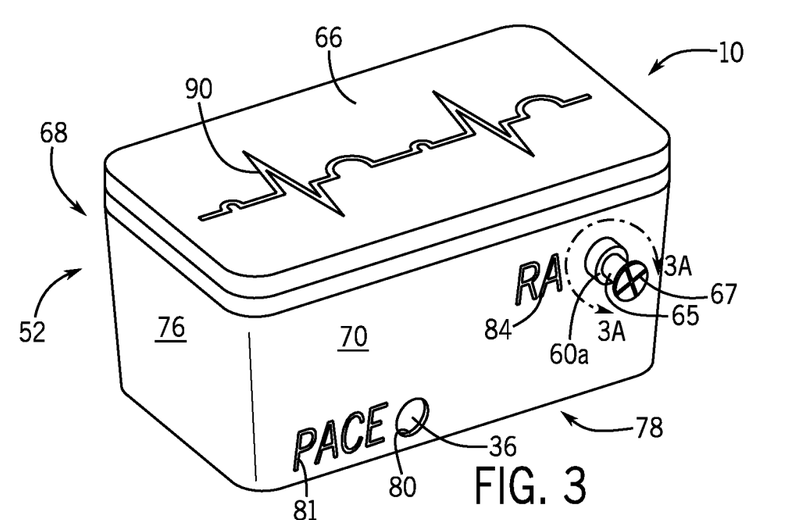
FIG. 3 is a perspective view of a right side of the adaptor showing a labeled terminal for connecting a pacemaker and a labeled terminal for connecting a right arm (RA) lead to a telemetry monitor cable.
Figures 3A, 4:
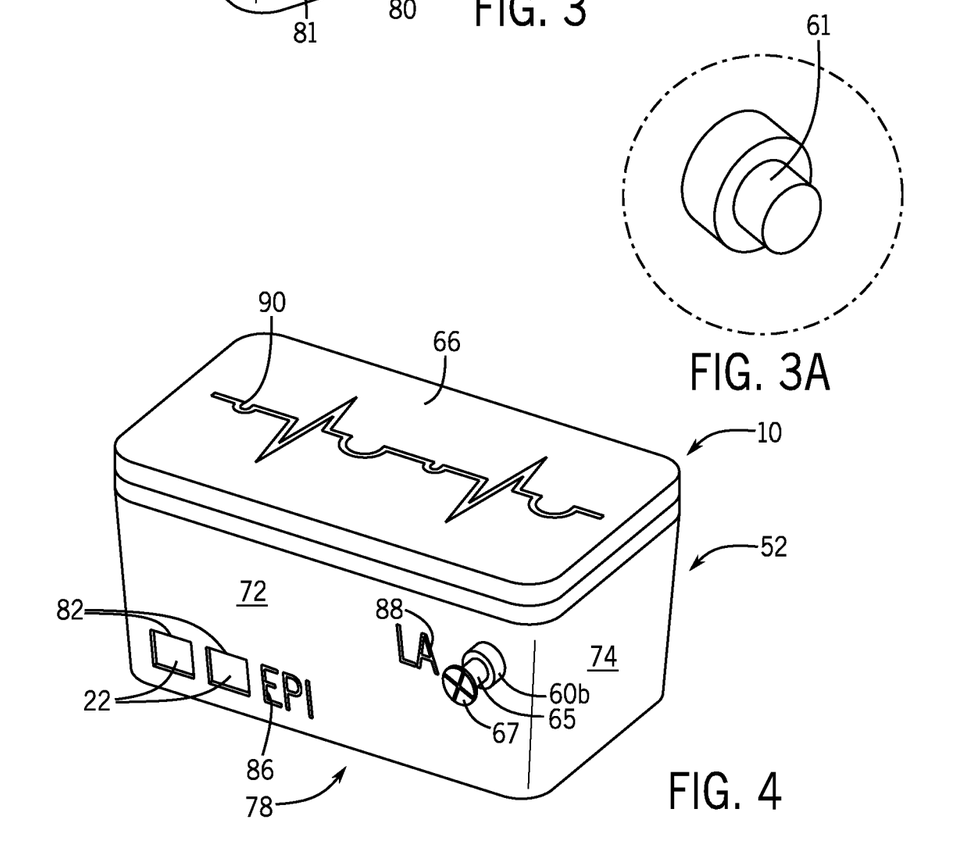
FIG. 3A is a perspective view of an alternative connector of the terminal connecting the RA lead.
FIG. 4 is a perspective view of a left side of the adaptor showing labeled terminals for connecting epicardial leads and a labeled screw terminal for connecting a left arm (LA) lead of the telemetry monitor cable.

Referring now to FIGS. 3 and 4, the multi-device connector block 10 may provide a housing 52, for example, having outer walls defining a rectangular inner volume 68 sealed from contamination. The housing 52 includes a bottom wall 78 joined on its right and left edges by upwardly extending right 70 and left 72 sidewalls, respectively, and joined on its top and bottom edges by upwardly extending top 74 and bottom 76 sidewalls, respectively. A top cover 66 is attachable over the inner volume 68 and may be permanently sealed, such as glued shut, to enclose the volume 68 or may be removable to allow access to the volume 68 containing the conditioning circuitry 54 therein. The top cover 66 may include a label 90, such as an ECG signal graphic or text label clearly denoting the function of the connector block 10 as an epicardial/pacer/monitor interconnection box. Different iterations of the device will allow variable designs of the block 10, such as a low profile device which can attach to the chest.

Referring now to FIGS. 2 and 4, the left sidewall 72 may include a pair of small openings 82 providing access to epicardial terminals 22 therein for connection of the epicardial pacing wires 20a, 20b. The epicardial terminals 22 may be a spring-loaded terminal allowing the wires to be engaged and disengaged by sliding into and out of the epicardial terminals 22. The epicardial terminals 22 are stabilized within the housing 52 for connection of the epicardial pacing wires 20a, 20b to the connector block 10. The epicardial terminals 22 are adapted to receive and grip the epicardial pacing wires 20a, 20b extending into the openings 82 and connect the wires to the conditioning circuitry 54 within the housing 52. It is understood that the epicardial terminals 22 may be any suitable wire connector such as terminal blocks, posts, crimp on connectors, insulation displacement connector, etc. connecting the epicardial pacing wires 20a, 20b to the internal conditioning circuitry 54.

The openings 82 for the epicardial pacing wires 20a, 20b may be labeled on the left sidewall 72 of the housing 52 with a label 86 to clearly indicate connection of epicardial pacing wires 20 to the epicardial terminals 22. The label 86 may use the term "EPI" or "EPICARDIAL" or another clearly recognizable term or abbreviation, representing connection of epicardial pacing wires 20a, 20b. Generally the label 86 may be any of a sticker, a decal, a label printed directly on the housing 52 or molded into the housing 52.

Referring now to FIGS. 2 and 3, the right sidewall 70 may include a small opening 80 allowing attachment therethrough of a pacemaker cable 34 (connecting the pulse generator 32) to pace terminals 36 of the connector block 10. The pace terminals 36 are stabilized within the housing 52 for connection of the pacemaker cable 34 to the connector block 10. The pacemaker cable 34 may be an industry standard connector, for example, Medtronic 5433 (Atrial) Cable, connecting the pulse generator 32 on one end to epicardial pacing wires 20 or electrodes on the other end. In the exemplary embodiment, the pacemaker cable 34 provides both positive wire 39a and negative wire 39b therein. The pace terminals 36 receive the wires 39a, 39b of the pacemaker cable 34 and separately conducts positive 39a and negative 39b wires to electrically couple the wires 39a, 39b to the internal conditioning circuitry 54 of the connector block 10 for delivery of the current pulse to the epicardial pacing wires 20a, 20b for pacing.

Generally, during bipolar pacing, a small electrical current is delivered by the pulse generator 32 to the negative pacing wire 39b, which travels through the connector block 10 to the negative epicardial pacing wire 20b, which delivers the current pulse to the heart 14. The returning current travels through the positive epicardial pacing wire 20a through the connector block 10 to the positive pacing wire 39a, which finally returns to the pulse generator 32 to complete the circuit. The pacemaker cable 34 may also receive atrial signals from the heart 14 (via epicardial pacing wires 20a, 20b placed on the heart 14 and delivering the atrial signals to the connector box 10), and deliver the atrial signals to the pulse generator 32 for analysis to determine a proper pacing prescription.

The opening 80 for the pacemaker cable 34 may be labeled on the right sidewall 70 of the housing 52 with a label 81 to clearly indicate connection of the pacemaker cable 34. The label 81 may use the term "PACE" or another clearly recognizable term representing connection of the pacemaker cable 34/pulse generator 32 and may be fabricated as discussed above.

Referring now to FIGS. 2, 3 and 4, in one embodiment, the sidewalls 70, 72 of the housing 52 also include electrically conductive bolts or screws 60a, 60b, respectively, threaded into the sidewalls 70, 72 with a tip 63 of the screws 60a, 60b extending into the housing 52 and a shank 65 and head 67 of the screw 60a, 60b extending outwardly from the housing sidewalls 72, 70. The screws 60a, 60b are electrically coupled to the internal conditioning circuitry 54, for example by soldering conductive wire between the internal conditioning circuitry 54 and the tips 63 of the screws 60a, 60b.

Electrical conductors 58a, 58b may be used to connect the screws 60a, 60b to a multichannel ECG monitor cable 40 of the telemetry monitoring system 24 allowing the conditioned epicardial signals to be viewed on the monitor 38. The electrical conductors 58a, 58b connecting the screws 60a, 60b to the multichannel monitor cable 40 may include conductive clips 56a, 56b, such as alligator clips, on theirs first ends allowing the electrical conductors 58a, 58b to clip onto the screws 60a, 60b. The second opposite ends of the electrical conductors 58a, 58b are connected to the multichannel monitor cable 40.

In an alternative embodiment, as seen in FIG. 3a, the screws 60a, 60b may be replaced with snaps 61, similar to buttons 64 found on surface electrodes 26, extending between an interior of the housing 52 and exterior of the housing 52 to conduct the conditioned epicardial signal through the snaps 61. The snaps 61 are attachable to fasteners 30 of normal ECG cables 28 (see FIG. 2) allowing the standard ECG cables 28 to be used instead of the electrical conductors 58a, 58b.

Referring now to FIG. 2, in the exemplary embodiment, the telemetry monitoring system 24 is a multichannel system that accepts a 5-electrode input with electrode positions at the RA, RL, LA, LL and chest positions. In this respect, the ECG monitor cable 40 of the telemetry monitoring system 24 includes a plurality of terminals 18 for receiving each of the 5-electrode inputs, i.e., RA, RL, LA, LL and chest. Typically, the respective surface ECG electrodes 26 are connected to each of the 5-electrode inputs. However, the variable surface electrode positions, such as the RA or LA, may be omitted and replaced by the electrical conductors 58a, 58b, respectively. In this iteration, the electrical conductor 58a delivers a signal output from the screw 60a to the RA surface electrode position and the electrical conductor 58b is attached to screw 60b, which is connected to ground, and connected at the LA surface electrode position. Thus, RA and LA terminals 18 of the ECG monitor cable 40 receive connections from the epicardial pacing wires 20a, 20b (via connector block 10) and the RL, LL and chest terminals 18 are connected directly to the respective surface ECG electrodes 26. It is understood that other surface electrode inputs could be utilized depending on the telemetry unit. For example, instead of RA or LA inputs, the chest terminal input may be used instead.

The right screw 60a extending outwardly from the right sidewall 70 may be labeled with a label 84 to clearly indicate that it may replace the RA connection of the multichannel monitor cable 40, such as with the letters "RA", and the left screw 60b extending outwardly from the left sidewall 72 may be labeled with a decal 88 to clearly indicate that it may replace the LA connection of the multichannel monitor cable 40, such as with the letters "LA".

It is understood that the telemetry monitoring system 24 may also accept 3-electrode and 12-electrode systems and similarly replace the RA and LA electrode positions with the epicardial pacing wires 20 (via connector block 10) and still simultaneously display the surface ECG electrodes 26 heart signals. For example, in a 3-electrode system the electrical conductors 58a, 58b representing epicardial pacing wires 20a, 20b are attached to the RA and LA electrode positions, respectively, and a surface ECG electrode 26 is connected to a LL electrode position on the patient 12.

Figure 5:
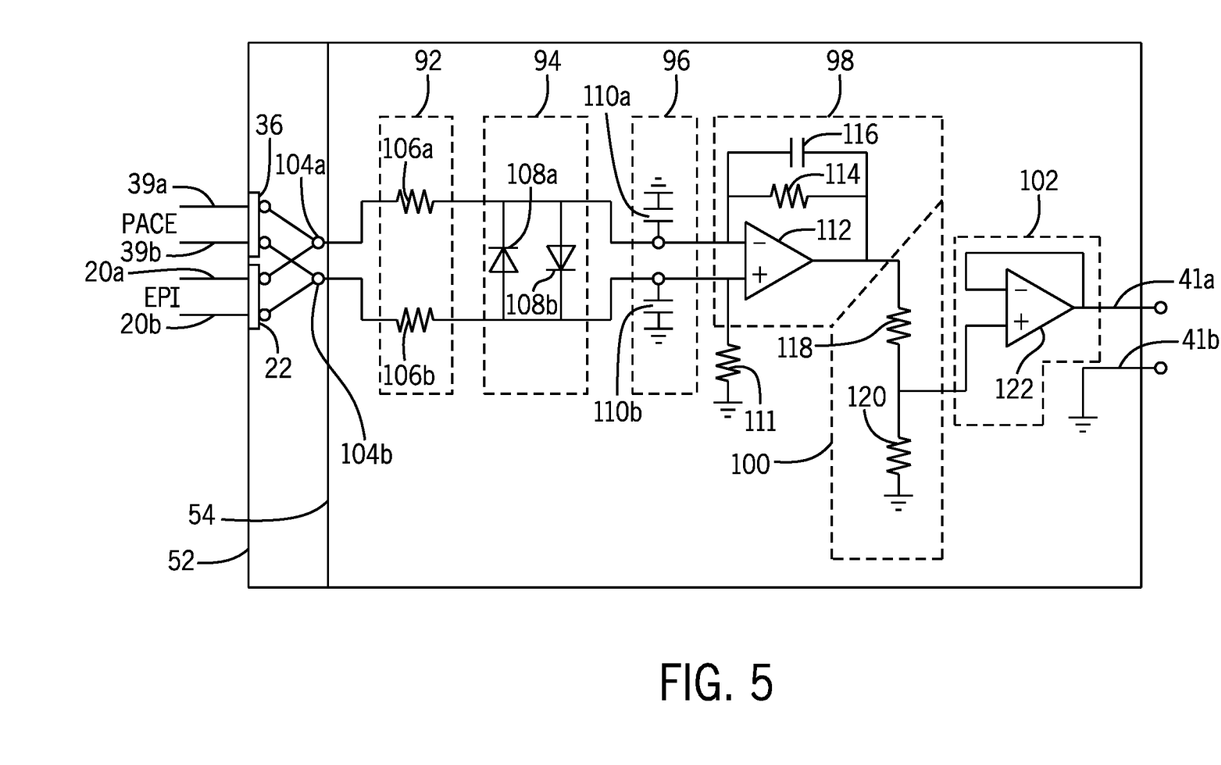
FIG. 5 is a schematic of the conditioning circuitry of the adaptor used to allow pacing output and to eliminate pacing artifact.

Referring now to FIG. 5, when atrial pacing and atrial visualization are performed simultaneously, pacing artifact can be seen on the monitor 38 as high magnitude pacing stimuli or spikes. In order to maintain the scale necessary to view the smaller atrial epicardial signals (in the lower mV range) compared to the much large pacing artifact (10-20 V range) the internal conditioning circuitry 54 of the connector block 10 processes the incoming epicardial signals before delivering them to the telemetry monitoring system 24. By reducing the pacing artifact, the monitor 38 is also protected from distortion, noise, and damage. The internal conditioning circuitry 54 attempts to preserve the incoming atrial epicardial signals as close to their original signal levels as possible.

As mentioned above, the positive 39a and negative 39b wires of the pacemaker cable 34 from the pulse generator 32 may be received at terminal 36 exposed through the housing 52 and connect respectively to junction points 104a and 104b on the circuitry 54 held within the housing 52. The same junction points 104a and 104b may also connect to epicardial terminals 22 exposed through the housing 52 and communicating with the epicardial pacing wires 20a and 20b.

Junction points 104a and 104b may connect to passive current limiting circuitry 92. For example, junction 104a connects to a first terminal of resistor 106a and junction 104b connects to a first terminal of resistor 106b. The resistors 106a, 106b are sized for example to be 10 kilo-ohms or larger to prevent undue loading on the pacer signals by the circuitry 54 thus providing input current limiting circuitry 92.

Following the current limiting circuitry 92, the signal is received by a first passive clipping circuit 94 that provides voltage protection of the internal conditioning circuitry 54 against high voltages of the pacing signal. Specifically, the remaining lead of resistor 106a provides a common juncture point with a cathode of diode 108a, an anode of diode 108b, one terminal of filter capacitor 110a, and a negative (inverting) input of operational amplifier 112. The remaining terminal of capacitor 110a connects to ground. Similarly the remaining lead of resistor 106b connects to an anode of diode 108a, a cathode of diode 108b, one terminal of filter capacitor 110b, and the positive (noninverting) input of operational amplifier 112. The remaining terminal of capacitor 110b connects to ground. The diodes 108a and 108b, thus connected back-to-back, provides a first passive clipping circuit 94 limiting the voltage to approximately the 0.7 volt conduction threshold of the diodes 108.

Following the first protective clipping circuit 94, a low pass filter 96 reduces the high voltage spikes of the pacer signal that occur before conduction of the diodes 108 before being passed onto the active clipping stage. For example, capacitors 110a, 110b together with the resistance of resistors 106a, 106b provide a low pass filter 96 having a frequency cut off of approximately 50 kilohertz.

Following the low pass filter 96, an active clipping circuit provides a gain block 98 that "clips" the high voltage spikes by boosting the gain of the incoming signal. Since the system supply reference voltage limits the overall signal amplitude to slightly below the supply reference voltage (e.g. approximately plus and minus 1.5 volts), the high voltage pacing artifact is cut off or "clipped" above the supply reference voltage. For example, the operational amplifier 112 has its noninverting input connected through resistor 111 to ground. The inverting input also connects to the output of the operational amplifier 112 through parallel connected resistor 114 and capacitor 116. These components are connected to provide a voltage stable gain of approximately 100 by the operational amplifier 112 providing gain block 98.

The amplifiers remain "saturated" so the top of the signal flattens out and remains flattened until the signal amplitude is decreased to below the supply reference voltage. The added gain provided by the operational amplifier 112 for the purpose of clipping is then removed for the purpose of restoring the signals to their proper level by using a division block 100 to divide the signal by a factor of 100 and bring it back down to its original value. For example, operational amplifier 112 is followed by a divider circuit comprised of series connected resistors 118 and 120 leading to ground. The junction of these resistors provides a divided voltage of approximately 100. These resistors 118 and 120 provide division block 100.

As noted, the effect of the successive application of gain block 98 and divider block 100 is to return the voltage received at the gain block back to the same voltage output from the divider block 100. The purpose of the successive operations is to boost the signal received by operational amplifier 112 beyond a compliance voltage range of that amplifier causing the amplifiers' fundamental limitations resulting from the voltage limits of its power rail to effectively clip the pacemaker signal at a desired voltage. For this purpose operational amplifier may be TLV 272 operational amplifier commercially available from Texas Instruments and having rapid recovery from clipping. Together gain block 98 and divider block 100 provide an active clipping circuit of high precision operating at a low voltage (the diodes below the level of 108 suitable for use with the present invention. The clipping provided by these blocks prevents the signal from the pacemaker from overwhelming the monitor 38 such as may provide a distorted signal, signal noise, or even monitor damage.

Following the voltage divider 100, an isolation amplifier 102 buffers the load provided by the monitor 38 for example preventing undue current from being diverted from the voltage divider 100. Specifically, a voltage at the junction of resistors 118 and 120 may be received by the noninverting input of operational amplifier 122 configured with its inverting input connected to its output to provide a unity gain buffer amplifier. The output of amplifier 122 provides leads 41a accessible through screw 60a to the monitor 38 with lead 41b accessible through screw 60b being reference to ground also provided to monitor 38.

The operational amplifiers 112 and 122 may be provided with electrical power from a contained battery or an appropriately isolated power supply as is generally understood in the art. The voltage provided to the operational amplifier 112 will desirably be regulated so as to provide an accurate clipping level for the circuit.

In operation, the connector box 10 is installed on or near the patient 12. The epicardial pacing wires 20a, 20b emerging from the puncture wound 48 in the chest of the patient 12 are inserted into the openings 82 of the left sidewall 72 of housing 52, labeled "EPI", providing access to the epicardial terminals 22. The wires 20a, 20b are attached to the epicardial terminals 22 coupling the wires 20a, 20b to the connector box 10. Then, the pacemaker cable 34 attached to the pulse generator 32 on one end is inserted into the opening 80 of the right sidewall 70 of the housing 52, labeled "PACE", providing access to the pace terminals 36. The pacemaker cable 34 is attached to the pace terminals 36 coupling the pacemaker cable 34 to the connector box 10. Finally, electrical conductors 58a, 58b are clipped or snapped onto screws 60a, 60b of the left 72 and right 70 sidewalls of the housing 52, labeled "RA" and "LA". The other end of the electrical conductors 58a, 58b are inserted into the RA and LA terminals 18, respectively, of the multichannel monitor cable 40 coupling the connector box 10 to the telemetry monitoring system 24. The medical professional may also install surface ECG electrodes 26 on the patient 12 at known ECG electrode positions on the body. ECG cables 28 may then be clipped or snapped onto the buttons 64 of the surface ECG electrodes 26 on one end and inserted into the respective terminals 18 (e.g., RL, LL, chest) of the monitor cable 40 on the other end.

Once the three connections are made to the connector box 10 of the epicardial paving wires 20a, 20b, pulse generator 32, and telemetry monitoring system 24, the medical professional may view the patient's cardiac signals on the monitor 38 of the telemetry monitoring system 24 to view the epicardial waveforms 44. If surface ECG electrodes 26 are coupled to the telemetry monitoring system 24, the medical professional may view the surface ECG electrode waveforms 46 and epicardial waveforms 44 simultaneously. During cardiac visualization, the medical professional may deliver pacing pulses to the patient 12 through the epicardial pacing wires 20a, 20b by initiating the appropriate prompts on the pulse generator 32. Simultaneous with and immediately after pacing, the medical professional may view the surface ECG electrode waveforms 46 and epicardial waveforms 44 on the monitor 38 to determine if additional pacing is needed in a quick and convenient manner.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference, which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context. When elements are indicated to be electrically connected, that connection may be direct or through an intervening conductive element.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

We claim:

1. A telemetry monitoring system, comprising:
   a pace generator providing electrical impulses configured to provide electrical pacing to a heart of a patient through epicardial pacing leads connected to the heart;
   a telemetry monitor configured to receive electrical cardiac signals from the epicardial pacing leads to provide a display of the electrical cardiac signals; and
   a connector box having
      first terminals configured to attach to the epicardial pacing leads;
      second terminals electrically connected to the first terminals and configured to attach to the pace generator;
      third terminals configured to attach to the telemetry monitor; and
      an electrical impedance providing a resistance mitigating pacing artifact between an electrical connection of the first and second terminals and the third terminals;
      wherein the electrical impedance permits display of the electrical cardiac signals on the telemetry monitor during electrical pacing of the heart.

2. The system of claim 1 wherein the electrical impedance provides a resistance of at least 10 kilo-ohms.

3. The system of claim 2 wherein the electrical impedance is a resistor.

4. The system of claim 1 wherein the electrical impedance attenuates the electrical impulses from the pace generator to allow display of the electrical cardiac signals by the telemetry monitor.

5. The system of claim 1 further comprising labels labeling the first, second and third terminals and containing indicia identifying connection of the epicardial pacing leads, pace generator, and telemetry monitor, respectively.

6. The system of claim 1 wherein the connector box has a weight and dimensions adapted to be supported on the body of the patient.

7. The system of claim 1 further comprising skin electrodes configured to be attached to the skin of the patient in electrical communication therewith and configured to attach to the telemetry monitor.

8. The system of claim 1 wherein the first, second and third terminals are mechanically releasable electrical connectors.

9. The system of claim 8 wherein the third terminals are studs of snaps.

10. The system of claim 8 wherein the third terminals are conductive screws.

11. A method of delivering electrical pacing to a patient and displaying cardiac signals from the patient simultaneously, the method comprising the steps of:
    providing a pace generator providing electrical impulses configured to provide electrical pacing to a heart of the patient through epicardial pacing leads connected to the heart; a telemetry monitor configured to receive electrical cardiac signals from the epicardial pacing leads to provide a display of the electrical cardiac signals; and a connector box having first terminals configured to attach to the epicardial pacing leads, second terminals electrically connected to the first terminals and configured to attach to the pace generator, third terminals configured to attach to the telemetry monitor, and an electrical impedance mitigating pacing artifact between an electrical connection of the first and second terminals and the third terminals wherein the electrical impedance permits display of the electrical cardiac signals on the telemetry monitor during electrical pacing of the heart;
    connecting the epicardial pacing leads to the first terminals;
    connecting the pace generator to the second terminals; and
    connecting the telemetry monitor to the third terminals;
    wherein the epicardial pacing leads, pace generator, and telemetry monitor are simultaneously connected to the connector box.

12. The method of claim 11 wherein the electrical impedance provides a resistance of at least 10 kilo-ohms.

13. The method of claim 12 wherein the electrical impedance is a resistor.

14. The method of claim 11 further comprising the step of connecting a distal end of the epicardial pacing leads to the heart of the patient.

15. The method of claim 14 further comprising the step of delivering electrical impulses to the heart.

16. The method of claim 15 further comprising the step of displaying the electrical cardiac signals on the telemetry monitor.

17. The method of claim 16 wherein the electrical pacing to the heart of the patient is simultaneous with the display of electrical cardiac signals on the telemetry monitor.

18. The method of claim 11 further comprising the step of placing surface electrodes on a chest of the patient.

19. The method of claim 18 further comprising the step of electrically connecting the surface electrodes to the telemetry monitor and displaying electrical cardiac signals from the surface electrodes on the telemetry monitor.

20. The method of claim 11 further comprising the step of attaching the connector box to a chest of the patient.

* * * * *